United States Patent
Klein et al.

(10) Patent No.: US 6,489,498 B2
(45) Date of Patent: Dec. 3, 2002

(54) SILANES WITH HYDROPHILIC GROUPS, THEIR SYNTHESIS AND USE AS SURFACTANTS IN AQUEOUS MEDIA

(75) Inventors: Klaus-Dieter Klein, Mülheim; Wilfried Knott, Essen; Götz Koerner, Essen; Manfred Krakenberg, Essen, all of (DE)

(73) Assignee: Th. Goldschmidt AG, Essen (DE)

( * ) Notice: Subject to any disclaimer, the term of this patent is extended or adjusted under 35 U.S.C. 154(b) by 0 days.

(21) Appl. No.: 09/818,419

(22) Filed: Mar. 27, 2001

(65) Prior Publication Data

US 2001/0018535 A1 Aug. 30, 2001

Related U.S. Application Data

(62) Division of application No. 08/301,372, filed on Sep. 6, 1994.

(30) Foreign Application Priority Data

Sep. 6, 1993 (DE) .......................... 43 30 059

(51) Int. Cl.$^7$ ................................. C07F 7/08
(52) U.S. Cl. .................. 556/413; 556/418; 556/428; 556/437; 556/438; 556/445; 556/449; 556/425; 556/423; 556/420; 556/419; 516/198; 516/200; 516/201; 516/204
(58) Field of Search ................. 556/413, 428, 556/438, 437, 418, 445, 449, 425, 423, 420, 419; 516/798, 200, 201, 204

(56) References Cited

U.S. PATENT DOCUMENTS

| | | | | |
|---|---|---|---|---|
| 4,654,161 A | * | 3/1987 | Kollmeier et al. | 556/413 X |
| 4,898,614 A | * | 2/1990 | Halloran et al. | 556/420 X |
| 5,159,095 A | * | 10/1992 | Celebuski | 556/449 X |
| 5,354,881 A | * | 10/1994 | Chang et al. | 556/419 |
| 5,430,167 A | * | 7/1995 | Klein et al. | 556/445 |
| 5,475,127 A | * | 12/1995 | Klein et al. | 556/445 |
| 6,252,029 B1 | * | 6/2001 | Amako et al. | 556/449 X |

FOREIGN PATENT DOCUMENTS

| | | |
|---|---|---|
| DE | 4141046 | 12/1991 |
| EP | 0367381 | 5/1990 |
| GB | 1520421 | 10/1975 |

OTHER PUBLICATIONS

Die Temperaturabhangigkeit der Benetzung, A.W. Neumann, et al. Aug. 1969, 5 pages.
Syntheses and Properties of Surfactants . . . , Hirohisa Maki, 1970, pp. 23–26, pp. 51–56.

* cited by examiner

Primary Examiner—Paul F. Shaver
(74) Attorney, Agent, or Firm—Frommer Lawrence & Haug LLP

(57) ABSTRACT

Silanes of the general formula

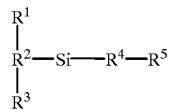

are prepared, wherein $R^1$, $R^2$ and $R^3$ in the molecule are the same or different and represent aliphatic or aromatic hydrocarbon groups, $R^4$ is a divalent hydrocarbon group with 4 to 12 carbon atoms and a lateral hydroxyl group, wherein the hydrocarbon group can be interrupted by an ether oxygen, $R^5$ is a hydrophilic, ionic group. A method for synthesizing these compounds is described. The silanes greatly lower the surface tension of aqueous solutions, the surface tension being reduced to values of about 23 mN/m. The silanes are biologically degradable and have pronounced surfactant properties.

7 Claims, No Drawings

SILANES WITH HYDROPHILIC GROUPS, THEIR SYNTHESIS AND USE AS SURFACTANTS IN AQUEOUS MEDIA

RELATED APPLICATIONS

This application is a divisional of application U.S. Ser. No. 08/301,372, now allowed, filed on Sep. 6, 1994, which, in turn, claims priority under 35 USC §119 to German application P 43 30 059 6, filed on Sep. 6, 1993.

FIELD OF INVENTION

The invention relates to novel silanes with hydrophilic groups, their synthesis and surfactants in aqueous media comprising the novel silanes. More particularly, it relates to silane surfactants, which are resistant to hydrolysis in acidic and alkaline media and significantly lower the surface tension of aqueous media. The concept of "aqueous" media is understood to include also those media which consist predominantly of water and additionally can contain water-soluble or water-miscible organic solvents.

BACKGROUND INFORMATION AND PRIOR ART

It is known from the state of the art that organo-modified siloxanes, such as polyether siloxanes or polysiloxanes, which have substituents with anionic, cationic or amphoteric groups, an appropriate structure and a balanced ratio of hydrophilic and hydrophobic groups, can lower the surface tension of aqueous solutions to a pronounced extent.

Surfactants with at least silicon atoms are disclosed in the German patent 41 41 046. They correspond to the general formula

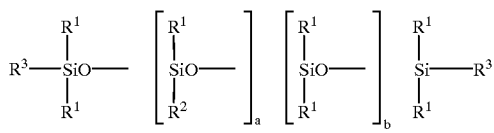

wherein $R^1$ is a methyl or phenyl group, with the proviso that at least 90% of the $R^1$ groups are methyl groups, $R^2$ is $R^1$ or —$(CH_2)_6$—$OSO_3^-.M^+$, wherein $M^+$ is an alkali, ½ alkaline earth or optionally an alkyl-substituted ammonium ion, $R^3$ is $R^1$ or $R^2$, with the proviso that in the average molecule, at least one $R^2$ or $R^3$ group is a —$(CH_2)_6$—$OSO_3^-.M^+$, a is 0 to 5, and b is 0 to 5.

The selected siloxane hexyl sulfates, which are trisiloxane hexyl sulfates in the event that three silicon atoms are present, bring about a pronounced lowering in the interfacial tension of neutral aqueous media to values of about 21 mN/m. However, they are unstable in acidic or alkaline solutions and, due to the hydrolysis of the Si—O—Si bonds and renewed condensation of the hydrolysis products to higher molecular weight oligomers, very rapidly lose their effectiveness and partly become insoluble in aqueous media.

Surfactants with a low content of silicon atoms are furthermore described in the European publication 0 367 381 (A2) and the British patent 1,520,421.

The European publication 0 367 381 (A2) relates to organosilicon compounds of the general formula

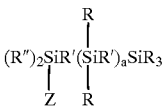

wherein the R groups, independently of one another, represent an alkyl, aryl, halogenated alkyl or halogenated aryl group with up to 18 carbon atoms, each R' groups represents an alkylene group, which separates adjacent silicon atoms by up to 6 carbon atoms from one another, and the R" groups independently of one another represent R or, when a=0, the $R_3SiR'$ group. Z is a hydrophilic substituent, which contains sulfur, nitrogen or phosphorus, a carboxy-functional group or the salt of such a group, while a has a value of 0, 1 or 2.

It follows from this that, by definition, the organosilicon group contains at least two silicon atoms. The synthesis of these carbosilanes is relatively expensive and is carried out, for example, by a reaction similar to a Grignard reaction. After that, carbosilane surfactants with a quaternary, sulfonate or betaine structure are synthesized by means of the hydrosilylation of, for example, allyl glycidyl ether or allylamine. The substances, so obtained, lower the surface tension of a 1% solution in distilled water to 23 to 25 mN/m.

Carbosilanes surfactants and their synthesis are disclosed in the British patent 1,520,421. They have the general formula

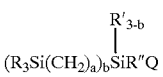

wherein R is a methyl, ethyl, propyl or trifluoropropyl group, with the proviso that at least 50% of the R groups are methyl groups, R' is an alkyl group with 1 to 6 carbon atoms and R" is a divalent aliphatic hydrocarbon group with 2 to 6 carbon atoms, which connects Q and the adjacent silicon atom by a bridge of at least 2 carbon atoms. Q is an —$O(C_2H_4O)_cX$, wherein c has a value of 3 to 12 and X is a hydrogen group, R''' group,

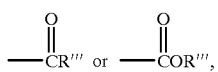

in which R''' is an alkyl group with 1 to 5 carbon atoms, a has a value or 1 or 2 and b a value of 2 or 3.

By definition, at least two silicon atoms must be present here also. In application tests, these compounds show remarkable foaming properties.

In this connection, it was known to those skilled in the art that, within groups of these known carbosilanes with comparable structure, the surfactant properties of the compounds deteriorate as the number of silicon atoms decreases, particularly from 4 to 3 or 2. This observation is reflected in the theory of Neumann (A. W. Neumann, D. Renzow, Zeitschrift f. Phys. Chem., New Issue 68, 11, (1969)), which states that the permethylated surface of the siloxane backbone is responsible for lowering the surface tension of aqueous solutions to below 30 to 40 mN/m.

Furthermore, reference is made to the Japanese publications of H. Maki et al. in YUKAGAGU 19, No. 4, page 51 ff. and YUKAGAGU 19, No. 11, page 23 ff., both from the year 1970, in which defined compounds of the formulas

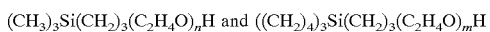

are described, wherein n=4.0 or 7.7 and m=10 or 17. However, these compounds lower the interfacial tension of a 0.1% by weight solution only to values of not less than 26.5 mN/m.

Likewise, quaternary nitrogen compounds having the formula

Bu$_3$M(CH$_2$)$_3$N$^+$(CH$_3$)$_3$Cl$^-$ (Bu=Butyl, M=Sn, Si), which, admittedly, are bacteriostatic but not very surface active, are described in these Japanese publications. The best representatives of these quaternary compounds lower the surface tension of a 1% aqueous solution to 32 mN/m.

The present invention is based on the surprising finding that, in contrast to general theoretical or factual knowledge, as expressed, for example, in the Neumann theory, selected silanes, that is, compounds with only a single silicon atom, but in which the ratio of hydrophilic to hydrophobic parts of the molecule is balanced, lower the surface tension of water exceeding effectively and, in contrast to the siloxane surfactants, are resistant to hydrolysis for days and weeks even in acidic and alkaline media. A further and not foreseeable advantage of the inventive silanes is their complete biodegradability, which makes them particularly suitable for use as surfactants. Such a profile of properties could not be derived from the state of the art and contradicts the previously customary assumptions concerning structural requirements, which organosilicon compounds should fulfill in order to show interfacial tension-lowering properties in aqueous systems.

OBJECT OF THE INVENTION

An object of the present invention is a novel silane. Another object of the invention is the synthesis of novel silanes. Yet another object of the invention is a surfactant in aqueous media comprising the novel silanes.

The silanes have the general formula

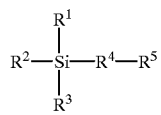

wherein

R$^1$, R$^2$ and R$^3$ in the molecule are the same or different and represent aliphatic or aromatic hydrocarbon groups,
R$^4$ is a divalent hydrocarbon group with 4 to 12 carbon atoms and a lateral hydroxyl group, wherein the hydrocarbon group can be interrupted by an ether oxygen, and
R$^5$ is a hydrophilic, ionic group.

Examples of preferred R$^1$, R$^2$ and R$^3$ groups are methyl, ethyl, propyl, butyl or phenyl groups. However, preferably only one of the R$^1$, R$^2$ and R$^3$ groups is a phenyl group. Preferably, at least 90% of the R$^1$, R$^2$ and R$^3$ groups are methyl groups.

The R$^4$ group is a divalent hydrocarbon group with 4 to 12 carbon atoms and a lateral hydroxyl group. This group is derived from an epoxide, which has an olefinic double bond, which can be hydrosilylated, and the epoxide ring of which has been opened. Diagrammatically, this can be shown by the following example:

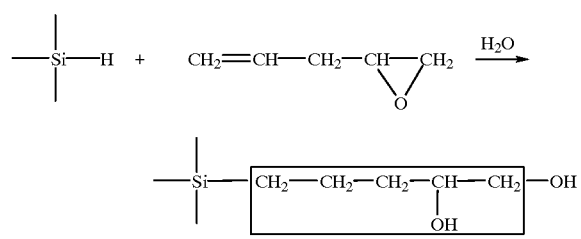

The group in the box corresponds to the R$^4$ group. Preferred examples of the R$^4$ group are:

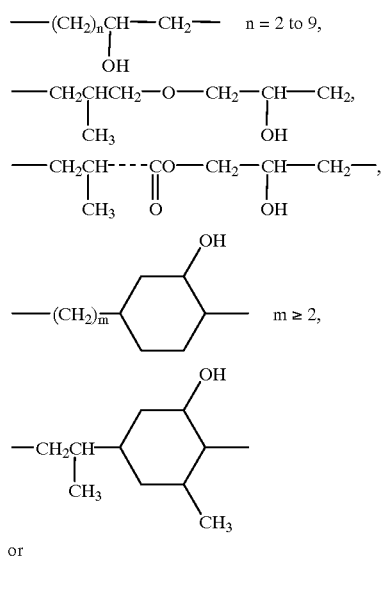

or

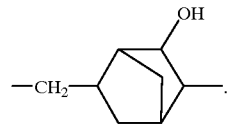

R$^5$ is an ionic group having the formula

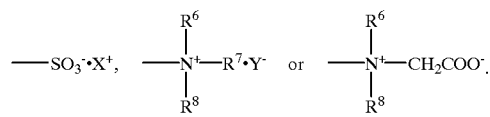

In the above, R$^6$, R$^7$ and R$^8$ are alkyl groups with 1 to 6 carbon atoms, which can be the same or different in the molecule. Examples of such groups are methyl, ethyl, propyl, butyl and the isobutyl group.

X$^+$ is a univalent cation and, moreover, usually a hydrogen, alkali, ½ alkaline earth or optionally a substituted ammonium ion. In particular, isopropyl-, triethyl-, butylmethyl-or octylammonium ions come into consideration as substituted ammonium ions.

Y$^-$ is any anion, preferably a halide or acetate ion. The chloride ion is preferred as halide ion.

The following compounds are examples of inventive silanes:

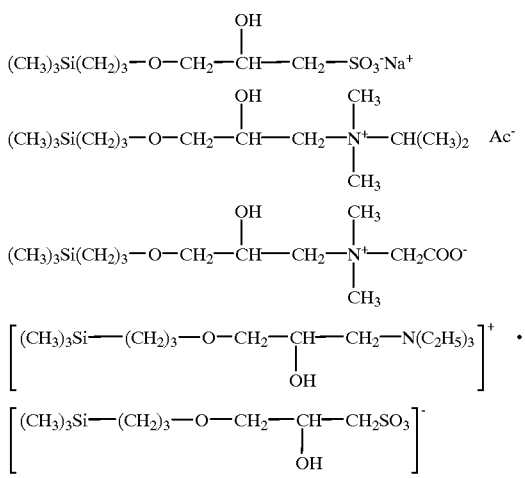

Yet another object of the invention is the synthesis of inventive compounds, which is characterized in that
a) epoxides, which have a olefinic double bond, are reacted by means of an addition reaction in the presence of a hydrosilylation catalyst with silanes of the general formula

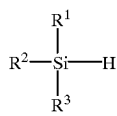

and
b) the epoxide ring of the silane-modified epoxides is opened by a known reaction and the product obtained is
b1) sulfonated, or
b2) quaternized by reaction with tertiary amines having the formula

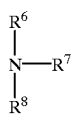

in the presence of an acid YH, or
b3) converted by a reaction with a compound of the formula

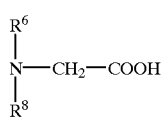

into the betaine.

Preferably, the hydrosilylation is carried out at an elevated temperature and/or in the presence of a solvent, a platinum catalyst being used as catalyst.

Step b1) of the method is carried out in a known manner by reacting the silane-modified epoxides with alkali sulfite/alkali hydrogen sulfate or by reacting the sulfite/hydrogen sulfate of the desired cation in the presence of a polar solvent. As solvent, an isopropanol/water mixture is preferably used. The reaction preferably is carried out at an elevated temperature, for example, at the boiling point of the isopropanol/water mixture.

Step b2) of the method, namely the reaction of silane-modified epoxides with different tertiary amines also is preferably carried out in the presence of a polar solvent, particularly a short-chain, low-boiling, aliphatic alcohol, such as isopropanol. The reaction proceeds in the presence of a protonic acid, acetic acid being preferred.

Step b3) of the method comprises the reaction of the silane-modified epoxides with dialkylaminoacetic acid in the presence of a polar solvent, particularly, a lower molecular weight aliphatic alcohol, such as isopropanol.

It is, of course, also possible to react the silane-modified epoxide initially with a dialkylamine, such as dimethylamine in an equivalent manner and then to convert the product obtained by reaction with sodium chloroacetate in the presence of a polar solvent, such as isopropanol, into the betaine.

It is well known to those skilled in the art that the critical micelle concentration (cmc) in aqueous solutions, which is an important parameter for characterizing the surfactant behavior of a compound, depends on the degree of bonding of the counterion to the rest of the surfactant. The cmc of the surfactant decreases as the bonding of the counterion to the rest of the surfactant increases. The degree of bonding depends on the polarizability, the valence and the hydrate shell of the counterion. The specific surfactant properties of a compound, such as the foaming and wetting capability, the solubility and the surface tension-lowering effect, are affected not only by the surfactant group, but also by the counterion.

It is also possible to have steps b1) and b2) of the method proceed simultaneously and to synthesize anion-cation surfactants, by carrying out the reaction of the product of step a) of the method with trialkylammonium hydrogen sulfite. The sulfonate, as well as the corresponding quaternary ammonium compound as a complex are then obtained in equimolar amounts. This is explained by the following reaction outline:

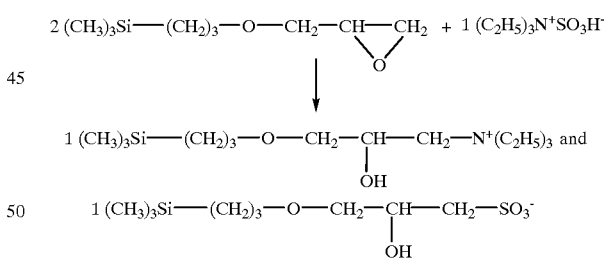

Yet another object of the invention is the use of the inventive silanes as surfactants in aqueous media. In this connection, it is possible to lower the surface tension of aqueous solutions to values of about 23 mN/m by the addition of 1% by weight of the inventive compounds. At the same time, the biological degradability of the inventive compound is of quite special significance. It is supplemented by the resistance of the silane surfactants to hydrolysis.

Important possible applications of the inventive silane surfactants are their use, for example,
as wetting agents:
in preparations for the treatment of plants (agricultural formulations); for improving the wetting of substrates with a low surface-free energy, such as polyethylene and polypropylene surfaces; for use in the paint industry; for the production of photographic films; in galvanizing technology;

as dispersant:

for dispersion paints, pigments and fillers;

as emulsifiers or additives in the textile industry for the production of textile auxiliaries, fabric softeners, lubricants, antistatic preparations; as a dyeing auxiliary;

as surfactants in general:

for use in fire extinguishers; as foam stabilizers; as surface-active additives to high speed printing inks, adhesives, dispersion adhesives, melt adhesives; for use in detergents; as additives for industrial cleaners;

as raw materials for use in cosmetics, for example, in grooming aids, shampoos, shower gels;

in technical applications and in the household:

anti-condensation agent for use in dishwashing detergents, laundry detergents, toilet cleaners, automatic gloss emulsions.

The preparation of the inventive compounds and their properties are described in greater detail in the following Examples, it being understood that the Examples are provided by way of illustration and not by way of limitation.

EXAMPLE 1

Preparation of Glycidyloxypropyltrimethylsilane

Allyl glycidyl ether (30.3 g, 0.266 moles) and 3 mg of platinum catalyst are weighed into a 300 mL laboratory autoclave. The autoclave, together with its contents, is cooled in an acetone/dry ice bath in an atmosphere of argon and 19.7 g of trimethylsilane (0.266 moles with a boiling point of 6.7° C.) are siphoned over from the condensed phase. The autoclave is closed and heated to 130° C. At the same time, the internal pressure increases to 7.6 bar and then drops again to 3.2 bar, indicating a reaction.

After the autoclave is cooled to room temperature and the pressure relieved, the contents are freed from platinum catalysts by filtration.

Epoxide oxygen: theoretical 8.5%, actual 8.4%

The $^{29}$Si-NMR and the $^{1}$H-NMR spectroscopic analyses reveal the following product structure:

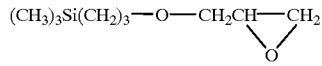

The product is freed from volatile components at 20° C. under the vacuum of an oil pump and is then used without further working up.

EXAMPLE 2

Reaction of Glycidylpropyltrimethylsilane with Dimethylaminoacetic Acid (Betaine)

Anhydrous dimethylaminoacetic acid (20.8 g, 0.2 moles) and 57.9 mL of isopropanol are added to a 250 mL 3-neck flask, which is equipped with stirrer, reflux condenser and dropping funnel, and heated to 50° C.

After that, 37.8 g of the glycidyloxy-propyltrimethylsilane (0.2 moles) prepared in Example 1, are slowly added dropwise.

At the end of the dropwise addition, stirring is continued for 6 hours under reflux. The product is then freed from solvent and volatile impurities in a rotary evaporator at 80° C. under the vacuum of an oil pump.

A white, powdery solid remains behind. Its 1% solution in distilled water spreads 10 mm on a polypropylene surface and it lowers the surface tension of water to a value of 22.8 mN/m.

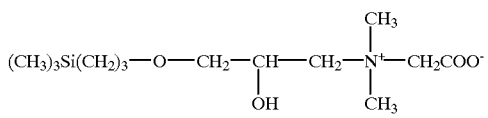

Table:

Lowering the Surface Tension as a Function of the Concentration of an Aqueous Solution

| Concentration (% by weight) | Surface Tension (mN/m) (T = 25° C.) |
|---|---|
| 1.0 | 22.8 |
| 0.5 | 23.6 |
| 0.4 | 27.5 |
| 0.3 | 28.6 |
| 0.2 | 31.8 |
| 0.1 | 35.3 |

EXAMPLE 3

Reaction of Glycidyloxypropyltrimethylsilane with Dimethylisopropylamine/Acetic Acid (Quat)

Glycidylpropyltrimethylsilane (19.67 g, 0.104 moles) is added dropwise to a mixture of 18.13 g of dimethylisopropylamine (0.208 moles), 6.25 g (0.104 moles) of acetic acid and 10.0 g of isopropanol at an internal temperature of 50° C. Stirring is then continued for a further hour at this temperature, a clear solution being obtained after a further hour. After a 5-hour post-reaction at the refluxing temperature, the reaction is concluded. The product is freed from solvent in the rotary evaporator under the vacuum of an oil pump and a temperature of 70° C. A clear, yellow-brown, viscous liquid (% nitrogen: 4.18 theoretical, 3.69 actual; % quaternary nitrogen: 4.18 theoretical, 3.61 actual).

According to the spectroscopy carried out, the product has the following general formula:

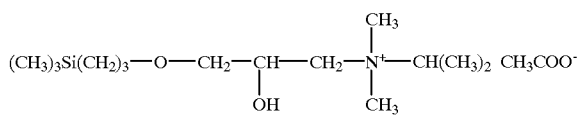

A 1% aqueous solution spreads 32 mm on polypropylene and shows a surface tension of 22.6 mN/m.

Table:

Surface Tension Lowering as a Function of the
Concentration of an Aqueous Solution

| Concentration (% by weight) | Surface Tension (mN/m) (T = 25° C.) |
|---|---|
| 1.0 | 22.6 |
| 0.5 | 25.7 |
| 0.4 | 26.3 |
| 0.3 | 27.0 |
| 0.2 | 28.8 |
| 0.1 | 31.6 |

EXAMPLE 4

Reaction of Glycidyloxypropyltrimethylsilane with Sodium Hydrogen Sulfite (Sulfonate)

Glycidyloxypropyltrimethylsilane (18.9 g, 0.1 moles), 24.12 g of water, 38.3 g of isopropanol and 2.52 g of sodium sulfite (0.02 moles) are added to a 250 mL 3-neck flask, which is equipped with a reflux condenser and a dropping funnel and heated under an atmosphere of nitrogen to the refluxing temperature. A 37% solution (22.5 g) of sodium thiosulfate in water is then added dropwise. At the end of the reaction, the pH of the reaction mixture is adjusted to a value of 7 by the addition of a solution of 10% by weight of acetic acid in distilled water and the mixture is subsequently filtered.

Volatile components are then distilled off in a rotary evaporator, initially at atmospheric pressure and later on under the vacuum of an oil pump, a temperature of 90° C. not being exceeded. At the same time, a white solid material is obtained, the 1% aqueous solution of which spreads 20 mm on a propylene film and has a surface tension of 25.9 mN/m.

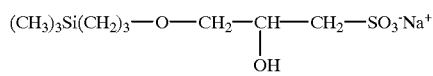

Table:

Surface Tension Lowering as a Function of the
Concentration of an Aqueous Solution

| Concentration (% by weight) | Surface Tension (mN/m) (T = 25° C.) |
|---|---|
| 1.0 | 25.9 |
| 0.5 | 26.8 |
| 0.3 | 27.9 |
| 0.2 | 28.8 |
| 0.1 | 30.0 |

EXAMPLE 5

Reaction of Glycidyloxypropyltrimethylsilane with Triethylammonium Hydrogen Sulfite (Cationic/Anionic Surfactant)

To 23.12 g (0.126 moles of triethylammonium hydrogen sulfite dissolved in 50 g of isopropanol in a 250 mL 3-neck flask, 47.5 g (0.252 moles) of glycidyloxypropyltrimethylsilane are added dropwise at an internal temperature of 30° C. The reaction mixture is then stirred for one hour, during which time it becomes clear. Subsequently, the reaction mixture is heated for 6 hours at the refluxing temperature.

After it is cooled, it is mixed with 1% by weight of bentonite A/J 10 and filtered. After that, the product is freed from volatile components under the vacuum of an oil pump at a waterbath temperature of 80° C.

A clear, viscous product is obtained, which dissolves in water to form a cloudy solution. The 1% solution in distilled water has a surface tension of 23 mN/m and spreads 30 mm on a polypropylene plate. Analytical investigations by means of $^1$H- and $^{13}$C-NMR spectroscopy confirm that the reaction product has the expected structure

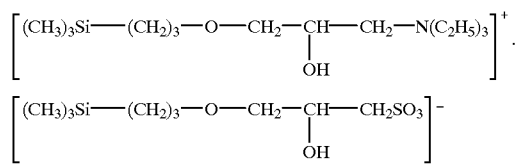

Table:

Surface Tension Lowering as a Function of the
Concentration of an Aqueous Solution

| Concentration (% by weight) | Surface Tension (mN/m) (T = 25° C.) |
|---|---|
| 1.0 | 23.0 |
| 0.5 | 24.5 |
| 0.4 | 24.9 |
| 0.3 | 25.9 |
| 0.2 | 30.1 |
| 0.1 | 36.7 |

Checking the Hydrolytic Stability of the Inventive Substances at pH 4, pH 7 and pH 12

The hydrolytic stability of the inventive products is demonstrated by way of example on 1% solutions in distilled water of the quat prepared in Example 3, as well as of the cationic/anionic surfactant prepared in Example 5.

To determine the wetting capability, the spreading of a 50 µL droplet of the 1% surfactant solution on a polypropylene film is measured over the maximum extent of the surface. Under these conditions, pure water has a blank value of 8 mm.

a) 1% aqueous solution of the quat:

| Storage (days) at room temperature | Spreading (mm) at | | | Appearance at the Solution |
|---|---|---|---|---|
| | pH 4 | pH 7 | pH 12 | |
| 0 | 60 | 32 | 30 | slightly cloudy |
| 5 | 65 | 25 | 25 | slightly cloudy |

-continued

| Storage (days) at room temperature | Spreading (mm) at | | | Appearance at the Solution |
|---|---|---|---|---|
| | pH 4 | pH 7 | pH 12 | |
| 10 | 60 | 25 | 25 | slightly cloudy |
| 15 | 60 | 25 | 25 | slightly cloudy |
| 60 | 70 | 30 | 20 | slightly cloudy | b) 1% Solution of the Cationic/Anionic Surfactant

| Storage (days) at room temperature | Spreading (mm) at | | | Appearance at the Solution |
|---|---|---|---|---|
| | pH 4 | pH 7 | pH 12 | |
| 0 | 30 | 30 | 25 | cloudy |
| 5 | 60 | 50 | 35 | cloudy |
| 10 | 60 | 28 | 30 | cloudy |
| 15 | 60 | 25 | 40 | cloudy |
| 60 | 40 | 40 | 30 | cloudy |

COMPARISON EXAMPLE

For comparison, a 1% aqueous solution of a siloxane sulfate ester having the average formula

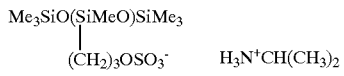

is included in the stability investigations:

| Storage (days) at room temperature | Spreading (mm) at | | | Appearance at the Solution |
|---|---|---|---|---|
| | pH 4 | pH 7 | pH 12 | |
| 0 | 40 | 30 | 35 | cloudy |
| 1 | / | 38 | 20 | cloudy |
| 2 | / | 40 | 10 | cloudy |
| 3 | / | 40 | 10 | cloudy |
| 4 | / | 40 | / | cloudy |
| 7 | / | 30 | / | cloudy |
| ≧14 | / | / | / | cloudy |

The investigation confirms the excellent resistance to hydrolysis of the inventive silane surfactants in contrast to the silane surfactants of the state of the art.

EXAMPLE 6

As described in Example 3, the reaction of the epoxysilane synthesized in Example 1 is carried out with ethylamine and dimethylaminoethanol.

Products with the following structures are obtained. The surfactant properties of the 1% by weight solutions of these substances are also listed below:

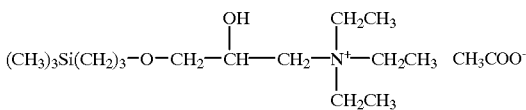

The surface tension of a 1% by weight aqueous solution is 22.7 mN/m and the spreading on polypropylene film is 20 mm.

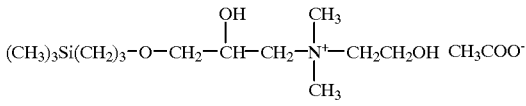

The surface tension of a 1% by weight aqueous solution is 25.1 mN/M and the spreading on polypropylene film is 10 mm.

EXAMPLE 7

By the method of Example 1, vinylcyclohexene oxide is reacted in an addition reaction with trimethylsilane. The resulting epoxysilane is then converted as in Example 3 by reaction with dimethylisopropylamine and acetic acid in isopropanol as solvent into the corresponding quat. A clear, yellow-brown liquid of low viscosity is obtained. According to the spectroscopy carried out, the product has the following formula:

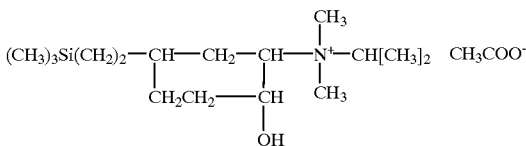

The surface tension of a 1% by weight aqueous solution of this substance is 33.5 mN/m and the spreading on polypropylene film is 11 mm, the low solubility of the product being striking.

We claim:

1. Silanes of the general formula

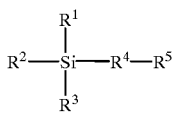

wherein $R^1$, $R^2$ and $R^3$ in a molecule are the same or different and represent aliphatic or aromatic hydrocarbon groups, $R^4$ is a divalent hydrocarbon group with 4 to 12 carbon atoms and a lateral hydroxyl group, wherein the hydrocarbon group can be interrupted by an ether oxygen, and $R^5$ is a hydrophilic, ionic group.

2. The silanes of claim 1, comprising that $R^1$, $R^2$ and $R^3$ can be alkyl groups with 1 to 4 carbon atoms, or one of these groups being a phenyl group.

3. The silanes of claim 2, comprising that at least 90% of the $R^1$, $R^2$ and $R^3$ groups being methyl groups.

4. The silanes of claims 1 or 2 comprising that $R^4$ is selected from the group consisting of

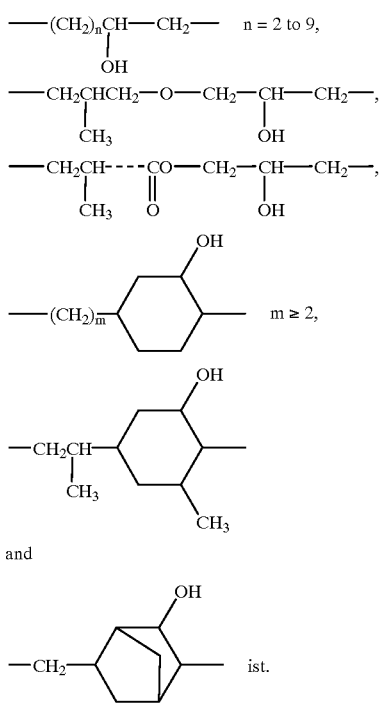

and

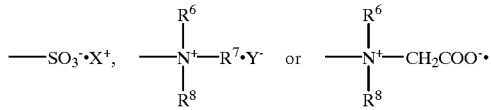

5. The silanes of claims 1 or 2, comprising that $R^5$ is

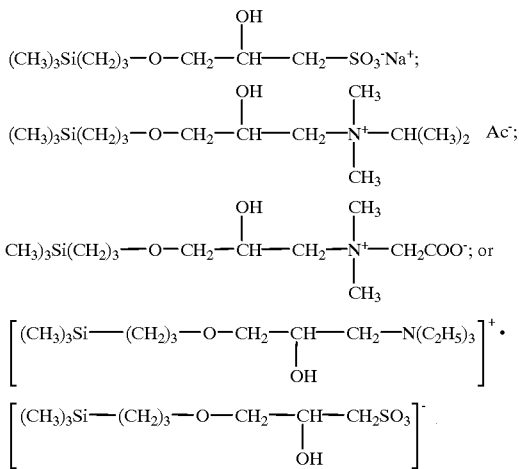

wherein $R^6$, $R^7$ and $R^8$ are alkyl groups with 1 to 6 carbon atoms, which can be the same or different in the molecule, $X^+$ is a hydrogen, alkali, ½ alkaline earth or an optionally substituted ammonium ion, and $Y^-$ is any ion, preferably a halide or acetate ion.

6. A biologically degradable, hydrolysis-resistant surfactant comprising the silanes of claim 1 in water-containing media.

7. The silane as claimed in claim 1, which has the formulae $(CH_3)_3Si(CH_2)_3-O-CH_2-\underset{OH}{CH}-CH_2-SO_3^-Na^+$;

$(CH_3)_3Si(CH_2)_3-O-CH_2-\underset{OH}{CH}-CH_2-\underset{\underset{CH_3}{|}}{\overset{\overset{CH_3}{|}}{N^+}}-CH(CH_3)_2 \quad Ac^-$;

$CH_3)_3Si(CH_2)_3-O-CH_2-\underset{OH}{CH}-CH_2-\underset{\underset{CH_3}{|}}{\overset{\overset{CH_3}{|}}{N^+}}-CH_2COO^-$; or $\left[(CH_3)_3Si-(CH_2)_3-O-CH_2-\underset{OH}{CH}-CH_2-N(C_2H_5)_3\right]^+ \cdot$ $\left[(CH_3)_3Si-(CH_2)_3-O-CH_2-\underset{OH}{CH}-CH_2SO_3\right]^-$

\* \* \* \* \*